US012768757B2

(12) United States Patent
Bugshan et al.

(10) Patent No.: US 12,768,757 B2
(45) Date of Patent: Oct. 20, 2026

(54) METHOD OF FIXATING TISSUE SAMPLE USING PROPOLIS-CONTAINING COMPOSITION

(71) Applicant: Imam Abdulrahman Bin Faisal University, Dammam (SA)

(72) Inventors: Amr S. Bugshan, Dammam (SA); Hawra A. Aljanobi, Dammam (SA); Asim M. Khan, Dammam (SA); Raghad A. Almunif, Dammam (SA); Rand R. Alshubaili, Dammam (SA); Sarah A. Khusheim, Dammam (SA); Nawal M. Alharbi, Dammam (SA); Muneer H. Alshuyukh, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 581 days.

(21) Appl. No.: 18/314,333

(22) Filed: May 9, 2023

(65) Prior Publication Data

US 2024/0377290 A1 Nov. 14, 2024

(51) Int. Cl.
*G01N 1/30* (2006.01)
*A61K 35/644* (2015.01)

(52) U.S. Cl.
CPC ............. *G01N 1/30* (2013.01); *A61K 35/644* (2013.01); *G01N 2001/307* (2013.01)

(58) Field of Classification Search
CPC ... G01N 1/30; G01N 2001/307; A61K 35/644
See application file for complete search history.

(56) References Cited

U.S. PATENT DOCUMENTS

| | | | | |
|---|---|---|---|---|
| 11,160,272 | B2 | 11/2021 | Postmes | |
| 2007/0003591 | A1 * | 1/2007 | Hesselbarth | A61L 31/16 424/539 |
| 2007/0140990 | A1 * | 6/2007 | Fetissova | A61K 8/8164 424/539 |
| 2013/0295181 | A1 * | 11/2013 | Brandao | A01N 65/00 424/539 |
| 2021/0120808 | A1 | 4/2021 | Herickhoff et al. | |

FOREIGN PATENT DOCUMENTS

| | | | | |
|---|---|---|---|---|
| CN | 105432600 | A | 3/2016 | |
| CN | 108392462 | A * | 8/2018 | A61K 8/988 |
| FR | 2 805 437 | A1 | 8/2001 | |
| FR | 3073125 | B1 * | 5/2020 | A01N 63/10 |
| IN | 202117037021 | A | 11/2021 | |
| RU | 2 123 259 | C1 | 12/1998 | |

OTHER PUBLICATIONS

Özkan, N. et al. "Honey as a substitute for formalin?." Biotechnic & Histochemistry 87.2 (2012): 148-153. (Year: 2012).*

Mavri et al. "Chemical properties and antioxidant and antimicrobial activities of Slovenian propolis." Chemistry & biodiversity vol. 9,8 (2012): 1545-58. doi:10.1002/cbdv.201100337 (Year: 2012).*

Alwahaibi, Nasar et al. "Effectiveness of neutral honey as a tissue fixative in histopathology." bioRxiv 2021.04.27.437988; doi: 10.1101/2021.04.27.437988 (Year: 2021).*

Attaporn Prueksakorn, et al., "The preservative effor of Thai propolis extract on the viability of human periodontal ligament cells", Dental Traumatology, vol. 32, Issue 6, Jul. 6, 2016, pp. 495-501.

Sandra Sobočanec, et al., "Oxidant/Antioxidant Properties of Croatian Native Propolis", Journal of Agricultural and Food Chemistry, vol. 54, No. 21, Sep. 27, 2006, pp. 8018-8026.

Ana Laura Carreño, et al., "Protective effect of Caffeic Acid Phenethyl Ester (CAPE) against oxidative stress", Journal of Functional Foods, vol. 29, 2017, pp. 178-184.

* cited by examiner

*Primary Examiner* — Anand U Desai
*Assistant Examiner* — Andrew T Moehlman
(74) *Attorney, Agent, or Firm* — Oblon, McClelland, Maier & Neustadt, L.L.P.

(57) ABSTRACT

A method of fixing a tissue sample includes treating the tissue sample with a propolis-containing composition to form a fixed tissue sample. The propolis-containing composition includes a propolis extract and at least one liquid. The propolis extract includes a resin and a wax. The at least one liquid includes propylene glycol and water, and the propolis-containing composition is an oil-in-water emulsion having an average particle size in a range of 5 to 200 nanometers (nm). The propolis extract is present in the propolis-containing composition at a concentration of 0.1 to 50 weight percentage (wt. %), based on a total of the propolis-containing composition. After the treating, the proteins in the pre-treatment composition of the tissue sample are crosslinked by resin and wax in the propolis extract.

16 Claims, 9 Drawing Sheets

0.9% Saline
(Group S)

12 hours 0.9% Saline
(Group S)

24 hours 0.9% Saline
(Group S)

48 hours 0.9% Saline
(Group S)

72 hours

10% Formalin
(Group F)

12 hours

10% Formalin
(Group F)

24 hours

10% Formalin
(Group F)

48 hours

10% Formalin
(Group F)

72 hours 6.6% Propolis
(Group P)

12 hours 6.6% Propolis
(Group P)

24 hours 6.6% Propolis
(Group P)

48 hours 6.6% Propolis
(Group P)

72 hours 6.6% Propolis
+10% Formalin
(Group P+F)

12 hours 6.6% Propolis
+10% Formalin
(Group P+F)

24 hours 6.6% Propolis
+10% Formalin
(Group P+F)

48 hours 6.6% Propolis
+10% Formalin
(Group P+F)

72 hours

METHOD OF FIXATING TISSUE SAMPLE USING PROPOLIS-CONTAINING COMPOSITION

STATEMENT REGARDING PRIOR DISCLOSURE BY THE INVENTORS

Aspects of this technology are described in "Propolis as a potential novel histological tissue fixative: A preliminary analysis" published in Applied Sciences, Volume 12, 9842, which is incorporated herein by reference in its entirety.

STATEMENT OF ACKNOWLEDGEMENT

This research was supported by the Imam Abdulrahman Bin Faisal University Institutional Review Board under the project IRB-2021-02-468.

BACKGROUND

Technical Field

The present disclosure is directed to a tissue fixation method, particularly a method of fixing a tissue sample using a propolis-containing composition.

Description of Related Art

The "background" description provided herein is to present the context of the disclosure generally. Work of the presently named inventors, to the extent it is described in this background section, as well as aspects of the description that may not otherwise qualify as prior art at the time of filing, are neither expressly nor impliedly admitted as prior art against the present invention.

Tissue fixation is an essential step for successful and precise microscopic interpretation. Tissue fixation is defined as a series of chemical processes that preserve tissue from deterioration and prevent it from autolysis (tissue destruction by enzymatic activity) and putrefaction (tissue breakdown by bacterial action). The tissue fixation before processing and staining is crucial to maintain the cellular morphology and composition as "lifelike" as possible by cross-linking the protein molecules to convert the tissue from a semi-liquid state to a semi-solid state. In addition, hardening the tissue specimen prevents its deterioration during preparation, facilitates its manipulation, and allows thin cutting (4-5 micrometers (μm)) before staining.

Tissue fixation can be achieved using physical and chemical methods. The major agents available for tissue fixation include aldehydes, oxidizing agents, alcohol-based agents, and metallic group fixative agents. An example of an aldehyde-based solution is 10% formalin, which consists of 3.7% formaldehyde in water with 1% methanol. It is a tissue fixative agent used worldwide owing to its commercial availability, ease of handling, low cost, and effective tissue preservation ability with minimal cellular disruption.

However, 10% formalin has some concerning toxic side effects, such as allergic reactions, skin irritation, and eye-burning sensation. Moreover, formaldehyde has potential human carcinogenicity that can cause nasopharyngeal cancer, myeloid leukemia, and brain tumors. Therefore, there is an urgent requirement to have a tissue fixative agent which is non-toxic and a safer and more effective natural substitute for formalin.

In view of the foregoing, it is one objective of the present disclosure to provide a method of fixing a tissue sample. A second objective of the present disclosure is to describe a propolis-containing composition for tissue fixation.

SUMMARY

In an exemplary embodiment, a method of fixing a tissue sample is described. The method includes treating the tissue sample having a pre-treatment composition with a propolis-containing composition to form a fixed tissue sample having a post-treatment composition. In some embodiments, the propolis-containing composition contains a propolis extract and at least one liquid. In some embodiments, the propolis extract contains a resin and a wax. In some embodiments, the pre-treatment composition contains a mixture of proteins, nucleic acids, carbohydrates, lipids, minerals, and vitamins. In some embodiments, the mixture of nucleic acids, carbohydrates, lipids, minerals, and vitamins in the pre-treatment composition is the same as that in the post-treatment composition. In some embodiments, the cellular structural integrity of the tissue sample maintains after the treating. In some embodiments, after the treating, two or more amino groups of the proteins in the pre-treatment composition of the tissue sample are crosslinked by the resin and wax in the propolis extract via two or more functional groups selected from the group consisting of an ester group (—COO—), a hydrocarbon group (—$CH_2$—), an alcohol group (—OH), and a carboxylic acid group (—COOH). In some embodiments, the propolis extract is present in the propolis-containing composition at a concentration of 0.1 to 50 weight percentage (wt. %), based on a total weight of the propolis-containing composition.

In some embodiments, the propolis extract is present in the propolis-containing composition at a concentration of 1 to 15 wt. %, based on the total weight of the propolis-containing composition.

In some embodiments, the propolis extract further contains at least one substance selected from the group consisting of an oil, a pollen, an amino acid, a minerals, a sugar, a B vitamin, a C vitamin, an E vitamin, a flavonoid, a phenol, an aromatic compound, and combinations thereof.

In some embodiments, the propolis extract further includes at least one substance selected from the group consisting of luteolin, 3-O—[(S)-2-methylbutyroyl] pinobanksin, 6-cinnamylchrysin, 8-[(E)-4-phenylprop-2-en-1-one]-(2R,3S)-2-(3,5-dihydroxyphenyl)-3,4-dihydro-2H-2-benzopyran-5-methoxyl-3,7-diol, 8-[(E)-4-phenylprop-2-en-1-one]-(2S,3R)-2-(3,5-dihydroxyphenyl)-3,4-dihydro-2H-2-benzopyran-5-methoxyl-3,7-diol, and 8-[(E)-4-phenylprop-2-en-1-one]-(2R,3S)-2-(3-methoxyl-4-hydroxyphenyl)-3,4-dihydro-2H-2-benzopyran-5-methoxyl-3,7-diol.

In some embodiments, the propolis extract contains one or more of the resin at a concentration of 40 to 80 wt. %. In some embodiments, the propolis extract contains one or more of the oil and wax at a concentration of 20 to 60 wt. %. In some embodiments, the propolis extract contains one or more of the pollen at a concentration of 1 to 20 wt. %. Each wt. % based on a total weight of the propolis extract.

In some embodiments, each of the resin and wax in the propolis extract has at least one first functional group, and at least one second functional group. In some embodiments, each of the at least one first functional group and the at least one second functional group is selected from the group consisting of an ester group (—COO—), a hydrocarbon group (—$CH_2$—), an alcohol group (—OH), and a carboxylic acid group (—COOH). In some embodiments, at least one first protein in the pre-treatment composition of the tissue sample is bonded to the resin and wax in the propolis extract via the at least one first functional group. In some embodiments, at least one second protein in the pre-treatment composition of the tissue sample is bonded to the same resin and wax in the propolis extract via the at least one second functional group.

In some embodiments, the at least one liquid includes one or more solvent selected from the group consisting of water, alcohol, glycol, glycerol, glycerin, glyceryl ether, diglycerol, and vegetable oil.

In some embodiments, the at least one liquid includes propylene glycol and vegetable glycerol. In some embodiments, a volume ratio of the propylene glycol to the vegetable glycerol is in a range of 20:1 to 1:20.

In some embodiments, the propolis-containing composition is in the form of at least one selected from the group consisting of a solution, an oil-in-water emulsion, a microemulsion, a capsule suspension, and a dispersion.

In some embodiments, the at least one liquid includes propylene glycol and water. In some embodiments, the propolis-containing composition is an oil-in-water emulsion having an average particle size in a range of 5 to 200 nanometers (nm).

In some embodiments, the propolis-containing composition further includes one or more additives selected from the group consisting of a fixative agent, an emulsifying agent, a buffering agent, a penetration enhancer, a crosslinking agent, a decalcifying agent, a salt, and a stabilizer.

In some embodiments, the fixative agent is at least one selected from the group consisting of formalin, glutaraldehyde, honey, syrup, and jaggery.

In some embodiments, the emulsifying agent is at least one selected from the group consisting of a cationic surfactant, an anionic surfactant, a non-ionic surfactant, and an amphoteric surfactant.

In some embodiments, the emulsifying agent includes a fatty alcohol sulfate, a fatty alcohol polyoxyalkylene ether, and a fatty acid alkanolamide.

In some embodiments, the buffering agent is at least one selected from the group consisting of sodium phosphate, sodium dihydrogen phosphate, and disodium hydrogen phosphate.

In some embodiments, the salt is at least one alkali metal halide selected from the group consisting of sodium chloride, potassium chloride, sodium bromide, potassium bromide, sodium iodide, and potassium iodide.

In some embodiments, the decalcifying agent is ethylenediaminetetraacetic acid (EDTA).

In some embodiments, the treating is for 1-72 hours, and forms a fixed tissue having enhanced preservation and fixation ability compared to a tissue sample treated with formalin.

In some embodiments, a ratio of the volume of the tissue sample to the volume of the propolis-containing composition is in a range of 1:1 to 1:20.

In some embodiments, the method further includes staining the fixed tissue sample with at least one stain selected from the group consisting of a hematoxylin and eosin stain, a reticulin stain, a trichrome stain, a periodic acid-schiff stain, a desmin stain, a TTF1 stain, a CD3 stain, and a PAX8 stain.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
FIG. 1A shows an image of a goat tongue, according to certain embodiments.

In the drawings, reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

According to an aspect of the present disclosure, a method of fixing a tissue sample is described. The method includes treating the tissue sample having a pre-treatment composition with a propolis-containing composition to form a fixed tissue sample having a post-treatment composition. In an embodiment, the tissue sample is in solid form having the same or different shapes, sizes, and orientations. In an embodiment, the tissue sample is from any animal. In still further embodiments, the tissue sample is collected via a biopsy puncher by punching out and stamping out pieces of tissue sample with defined diameter and length. In some embodiments, the tissue sample has a diameter in a range of 1 to 20 millimeters (mm), preferably 3 to 15 mm, preferably 5 to 10 mm, or even more preferably about 8 mm. In some further embodiments, the tissue sample has a length in a range of 5 to 100 mm, preferably 10 to 80 mm, preferably 20 to 60 mm, or even more preferably about 40 mm. Other ranges are also possible. As used herein, animal refers to multi-cellular vertebrate organisms, a category that includes, for example, mammals and birds. The term mammal includes both human and non-human mammals. Similarly, the term "subject" includes both human and veterinary subjects, for example, humans, non-human primates, goats, dogs, cats, horses, and cows. In an embodiment, the tissue sample is obtained from a deceased subject. In an embodiment, the tissue is connective tissue, epithelial tissue, muscle tissue, and/or nervous tissue. In an embodiment, the tissue is collected from any part of the subject, including but not limited to the tongue, lips, salivary glands, parotid glands, submandibular glands, sublingual glands, pharynx, esophagus, stomach, small intestine, duodenum, jejunum, ileum, large intestine, cecum, ascending colon, transverse colon, descending colon, sigmoid colon, rectum, liver, gallbladder, mesentery, pancreas, anal canal, nasal cavity, pharynx, larynx, trachea, bronchi, bronchioles, lungs, kidneys, ureter, bladder, urethra, ovaries, fallopian tubes, uterus, cervix, testes, epididymis, vas deferens, seminal vesicles, prostate, bulbourethral glands, pituitary gland, pineal gland, thyroid gland, parathyroid glands, adrenal glands, pancreas, heart, lymph node, bone marrow, thymus, spleen, tonsils, cerebrum, cerebral hemispheres, diencephalon, the brainstem, midbrain, medulla oblongata, cerebellum, eye, cornea, iris, ciliary body, lens, retina, ear, outer ear, earlobe, eardrum, middle ear, ossicles, inner ear, cochlea, olfactory epithelium, mammary glands, skin, subcutaneous tissue, ligaments, or tendons. In an embodiment, the tissue is from a tumor. In an embodiment, the tumor may include but is not limited to sarcomas and carcinomas, including fibrosarcoma, myosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyngioma, ependymoma, pinealoma, hemangioblastoma, acoustic neuroma, oligodendroglioma, meningioma, melanoma, neuroblastoma and retinoblastoma).

The tissue sample is treated with the propolis-containing composition for 1-120 hours, preferably 12-96 hours, preferably 24-72 hours, or even more preferably about 48 hours. Other ranges are also possible. In some embodiments, the propolis-containing composition has as an absolute viscosity of about 5 centipoises (cP) to about 2000 cP at 25° C., preferably 20 to 1500 cP, preferably 50 to 1000 cP, preferably 100 to 700 cP, or even more preferably about 200 to 400 cP, as measured using a cone-and-plate viscometer. The propolis-containing composition includes the propolis extract. The propolis extract is present in the propolis-containing composition at a concentration of 0.1 to 50 weight percentage (wt. %), preferably 1-15 wt. %, or even more preferably about 10 wt. % based on a total of the propolis-containing composition. Propolis extract is an extract of propolis. Propolis, also known as "bee glue", is a natural resinous material produced by bees from substances in plants and flower buds. The hue of propolis varies according to the region and the plant it originates from. Its diverse types have a wide melting range of 60-100° C., preferably 70-90° C., or even more preferably about 80° C. Other ranges are also possible. It is rigid at low temperatures and pliable at high temperatures; unlike solvents such as water and oil, alcohol solvent, such as ethanol, dissolves the primary biologically active components of propolis. The propolis extract may be a solid, and the solid may be in the form of powder, particles, liquid, or a gel.

The propolis extract of the propolis-containing composition includes a resin and a wax. In some embodiments, the propolis extract further includes at least one substance selected from the group consisting of an oil, a pollen, an amino acid, a minerals, a sugar, a B vitamin, a C vitamin, an E vitamin, a flavonoid, a phenol, an aromatic compound, and combinations thereof. In some embodiments, the propolis extract includes resin, oil and wax, and pollen, as well as chemical elements such as organic compounds such as steroids, amino acids, and polyphenols [Easton-Calabria, A.; Demary, K. C.; Oner, N. J. Beyond Pollination: Honey Bees (*Apis mellifera*) as Zootherapy Keystone Species. Front. Ecol. Evol. 2019, 6, 161, which is incorporated herein by reference in its entirety]; minerals; carbohydrates; vitamins B, C, and E; flavonoids. In some embodiments, the propolis extract includes one or more resins at a concentration of 40 to 80 wt. % based on the total weight of the propolis extract, preferably 50 to 70 wt. %, or even more preferably about 60 wt. % based on the total weight of the propolis extract. In some embodiments, the one or more oils, and waxes are present in the propolis extract at a concentration of 20 to 60 wt. %, preferably 30 to 50 wt. %, or even more preferably about 40 wt. % based on the total weight of the propolis extract. In some further embodiments, the one or more pollens are present in the propolis extract at a concentration of 1 to 20 wt. %, preferably 5 to 15 wt. %, or even more preferably about 10 wt. %, based on the total weight of the propolis extract. The variations in the above constituents' concentration determine propolis' properties [Mavri, A.; Abramovič, H.; Polak, T.; Bertoncelj, J.; Jamnik, P.; Možina, S. S.; Jeršek, B. Chemical Properties and Antioxidant and Antimicrobial Activities of Slovenian Propolis. Chem. Biodivers. 2012, 9, 1545-1558, which is incorporated herein by reference in its entirety]. In some embodiments, the pollen is at least one of tree pollen, grass pollen, and weed pollen. In some embodiments, the pollen is at least one of inaperturate pollen, aperturate pollen, and pollen aggregate. In further some embodiments, the pollen has an average particle size in a range of 10 to 200 micrometers (μm) preferably 20 to 100 μm, preferably 30 to 80 μm, or even more preferably 40 to 60 μm. Other ranges are also possible. The stickiness of the propolis extract may protect tissue samples from the invasion of various pathogens (putrefaction) and reinforce cellular structural integrity. Furthermore, a mixture of natural resins and waxes in the propolis extract may contribute to the crosslinking of tissue molecular proteins, which accelerates and enhances the tissue fixation ability. Organic compounds, by their scavenging action, prevent tissue putrefaction and autolysis due to their antimicrobial and antioxidant effects, and this may also improve propolis fixation properties.

The propolis extract further includes at least one substance selected from the group consisting of luteolin, 3-O—[(S)-2-methylbutyroyl]pinobanksin, 6-cinnamylchrysin, 8-[(E)-4-phenylprop-2-en-1-one]-(2R,3S)-2-(3,5-dihydroxyphenyl)-3,4-dihydro-2H-2-benzopyran-5-methoxyl-3,7-diol, 8-[(E)-4-phenylprop-2-en-1-one]-(2S,3R)-2-(3,5-dihydroxyphenyl)-3,4-dihydro-2H-2-benzopyran-5-methoxyl-3,7-diol, and 8-[(E)-4-Phenylprop-2-en-1-one]-(2R,3S)-2-(3-methoxyl-4-hydroxyphenyl)-3,4-dihydro-2H-2-benzopyran-5-methoxyl-3,7-diol.

The propolis-containing composition includes at least one liquid. In some embodiments, at least one liquid includes one or more solvents selected from the group consisting of water, alcohol, glycol, glycerol, glycerin, glyceryl ether, diglycerol, and vegetable oil. In another embodiment, the at least one liquid includes propylene glycol and vegetable glycerol. In a preferred embodiment, a volume ratio of the propylene glycol to the vegetable glycerol is in a range of 20:1 to 1:20, preferably 15:1 to 1:15, preferably 10:1 to 1:10, preferably 1:5 to 5:1, or even more preferably about 1:1. Other ranges are also possible. In a more preferred embodiment, the liquid includes propylene glycol and water.

The propolis-containing composition further includes one or more additives selected from the group consisting of a fixative agent, an emulsifying agent, a buffering agent, a penetration enhancer, a crosslinking agent, a decalcifying agent, a salt, and a stabilizer. The fixative agent is at least one selected from the group consisting of formalin, glutaraldehyde, honey, syrup, and jaggery. Generally, formalim is used as a fixative agent. In some embodiments, the fixative agent is present in the propolis-containing composition at a concentration of 0.1 to 20 wt. %, based on the total weight of the propolis-containing composition, preferably 5 to 15 wt. %, or even more preferably about 10 wt. % based on the total weight of the propolis-containing composition. Other ranges are also possible.

The emulsifying agent is at least one selected from the group consisting of a cationic surfactant, an anionic surfactant, a non-ionic surfactant, and an amphoteric surfactant. The emulsifying agent includes one or more of sulfate of fatty alcohol, polyoxyalkylene ether of fatty alcohol, and alkanolamide of fatty acid. The buffering agent includes one or more of sodium phosphate, sodium dihydrogen phosphate, disodium hydrogen phosphate, or a combination thereof. The salt includes one or more of an alkali metal halide, and where the alkali metal halide is at least one selected from the group consisting of sodium chloride, potassium chloride, sodium bromide, potassium bromide, sodium iodide, and potassium iodide. In some embodiments, other salts such as aluminum chloride, sodium fluoride, iron chloride, zinc sulfate, and lead thiocyanate may be used as well. Generally, metal salts improve the immunohistochemical staining ability of tissue samples to a greater extent than de-ionized water. In one embodiment, the decalcifying agent is ethylenediaminetetraacetic acid (EDTA). Other suitable examples of decalcifying agents include but are not limited to EGTA, CDTA, EDADP-X, EDADP-B, EDDRA, DFA, PPi, EDTP-B and EDTP-X. In some embodiments, the propolis-containing composition may optionally include a dye or other substances that do not significantly contribute to the function of the composition. These substances may be added to allow easy identification of the composition or to improve the odor of the composition.

Buffering agents useful in the composition include, but are not limited to, citric acid, tartrate salts, phthalate salts, borate salts, tris(hydroxymethyl)aminomethane (Tris-HCl), EDTA and phosphate salts. The choice of the buffer is dependent on the desired pH range of the composition. By choosing the appropriate buffer the pH of the composition may be altered to values ranging from about 1 to 11. The pH of the composition is preferably maintained between about 4 and 10 more preferably between about 5 and 8. Other ranges are also possible.

In some embodiments, the propolis-containing composition is in the form of a solution, an oil-in-water emulsion, a micro-emulsion, a capsule suspension, and/or a dispersion. In some further embodiments, the propolis-containing composition is an oil-in-water emulsion. As used herein, an "oil-in-water" emulsion refers to an oil-in-water mixture in which the water forms a continuous phase and the oil is in discontinuous droplets. In some further preferred embodiments, the oil-in-water emulsion has an average particle size in a range of 5 to 200 nanometers (nm), preferably 50 to 150 nm, or even more preferably about 100 nm. In yet some other embodiments, the oil-in-water emulsion has an average particle size in a range of 200 to 1000 nm, preferably 400 to 800 nm, or even more preferably about 600 nm. Other ranges are also possible.

In some embodiments, the pre-treatment composition of the tissue sample contains a mixture of proteins, nucleic acids, carbohydrates, lipids, minerals, and vitamins. In some embodiments, the mixture of nucleic acids, carbohydrates, lipids, minerals, and vitamins in the pre-treatment composition is the same as that in the post-treatment composition. In some preferred embodiments, the cellular structural integrity of the tissue sample maintains after the treating. After the treating, two or more amino groups of the proteins in the pre-treatment composition of the tissue sample are cross-linked by the resin and wax in the propolis extract via two or more functional groups selected from the group consisting of an ester group (—COO—), a hydrocarbon group (—$CH_2$—), an alcohol group (—OH), and a carboxylic acid group (—COOH);

Treating the tissue-sample with the propolis-containing composition does not alter the composition of nucleic acids, carbohydrates, and lipids in the tissue sample. As used herein, the term "does not alter the composition" indicates that the percentage composition of the nucleic acids, carbohydrates and lipids remains more than 60%, preferably 70% more preferably 80%, yet more preferably 90%, and yet more preferably greater than 95%, identical, before treating the tissue sample with the popolis-containing composition. The term "Nucleic acid" includes, but is not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. In an embodiment, a quantity of DNA in the fixed tissue sample is higher than the same tissue sample fixed with formalin. In an embodiment, a quantity of DNA in the fixed tissue sample is within 5%, preferably 4%, 3%, 2%, or 1% of the tissue sample fixed with formalin. In an embodiment, a quantity of RNA in the fixed tissue sample is higher than the same tissue sample fixed with formalin. In an embodiment, a quantity of RNA in the fixed tissue sample is within 5%, preferably 4%, 3%, 2%, or 1% of the tissue sample fixed with formalin. In an embodiment, a purity of RNA and DNA in the fixed tissue sample is within 5%, preferably 4%, 3%, 2%, or 1% of the tissue sample fixed with formalin.

The term "lipid" is used in accordance with its ordinary meaning in chemistry and refers to a hydrophobic molecule which is typically characterized by an aliphatic hydrocarbon chain. In embodiments, the lipid includes a carbon chain of 3 to 600 carbon atoms, preferably 50 to 500 carbon atoms, preferably 100 to 450 carbon atoms, preferably 150 to 400 carbon atoms, preferably 200 to 350 carbon atoms, or even more preferably about 250 to 300 carbon atoms. Other ranges are also possible.

The term "carbohydrate" refers to a group of organic compounds occurring in living tissues and foods in the form of starch, cellulose, and sugars. The ratio of oxygen and hydrogen in carbohydrates is the same as in water, that is, 2:1. As used herein, carbohydrates include monosaccharides, disaccharides, and polysaccharides.

The proteins in the tissue sample are crosslinked by each of the resin and wax in the propolis extract having at least one first functional group, and at least one second functional group. The proteins refer to a polymer of amino acid residues.

The propolis extract includes several substances, such as resins, one or more oils and waxes, one or more pollens, one or more amino acids, one or more minerals, one or more sugars, one or more vitamins B, one or more vitamins C, one or more vitamins E, one or more flavonoids, one or more phenols, and one or more aromatic compounds. Each of these substances includes several functional groups, such as —COOH, —OH, —$NH_2$, —CN, —SH, etc., which can bind to one or more proteins in the tissue sample. In some embodiments, each of the at least one first functional group and the at least one second functional group of the resin and wax is selected from the group consisting of an ester group (—COO—), a hydrocarbon group (—$CH_2$—), an alcohol group (—OH), and a carboxylic acid group (—COOH). Similarly, the tissue sample may include one or more first protein(s), and one or more second protein(s). In some embodiments, at least one first protein in the pre-treatment composition of the tissue sample is bonded to the resin and wax in the propolis extract via the at least one first functional group, and at least one second protein in the pre-treatment composition of the tissue sample is bonded to the same resin and wax in the propolis extract via the at least one second functional group.

In some embodiments, at least 60% of protein molecules based on a total number of the protein molecules in the pre-treatment composition are crosslinked by the propolis extract after the treating, preferably at least 60%, preferably at least 70%, preferably at least 80%, preferably at least 90%, or even more preferably at least 95% of the protein molecules are crosslinked. In some further embodiments, at least 50% of protein molecules based on the total number of the protein molecules in the pre-treatment composition are crosslinked by the propolis extract after the treating for 1-24 hours to form the fixed tissue sample having a post-treatment composition, preferably at least 60%, preferably at least 70%, preferably at least 80%, or even more preferably at least 90% of the protein molecules are crosslinked by the propolis extract, each % based on the total number of the protein molecules in the pre-treatment composition. In some preferred embodiments, the proteins in the post-treatment composition after crosslinking has an average molecular weight of at least 1 time, at least 3 times, at least 5 times, at least 10 times, at least 30 times, or even more preferably at least 50 times higher than that of the proteins in the pre-treatment composition. In some more preferred embodiments, the proteins in the post-treatment composition after crosslinking has an average molecular weight of no more than 60 times, no more than 40 times, no more than 20 times, no more than 10 times, or even more preferably no more than 5 times higher than that of the proteins in the pre-treatment composition. Other ranges are also possible.

Figure 8A:
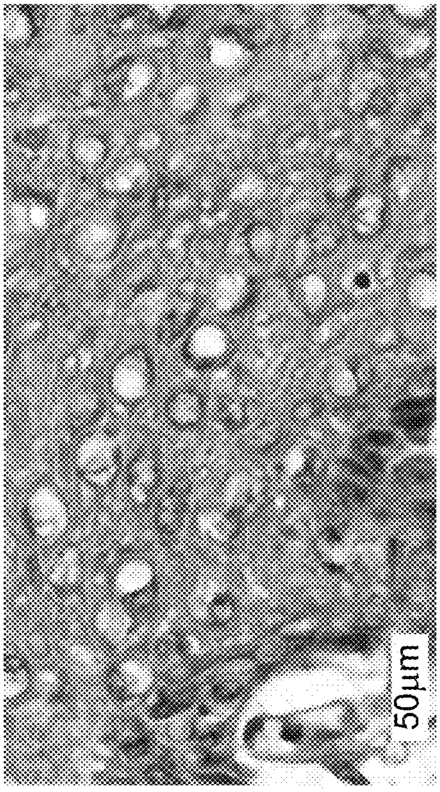
FIG. 8A is a photomicrograph of hematoxylin-eosin-stained section depicting a lower ⅓$^{rd}$ portion of epithelium at 48 hours (40×) in 0.9% saline, according to certain embodiments.
Figure 8B:
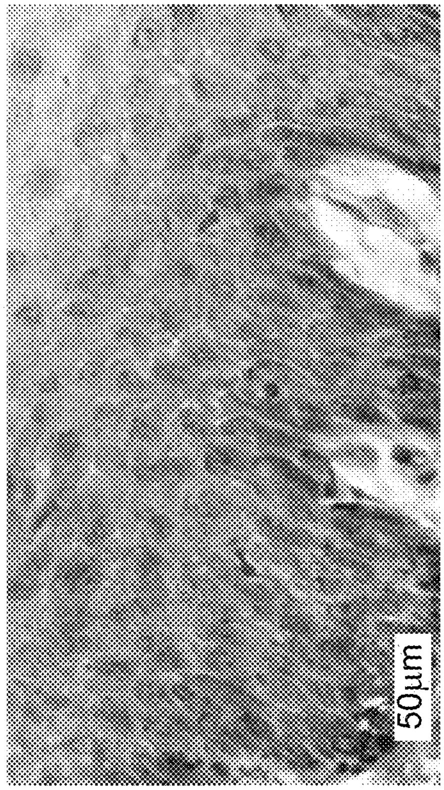
FIG. 8B is a photomicrograph of the hematoxylin-eosin-stained section depicting a lower ⅓$^{rd}$ portion of epithelium at 48 hours (40×) in 10% formalin according to certain embodiments.
Figure 8C:
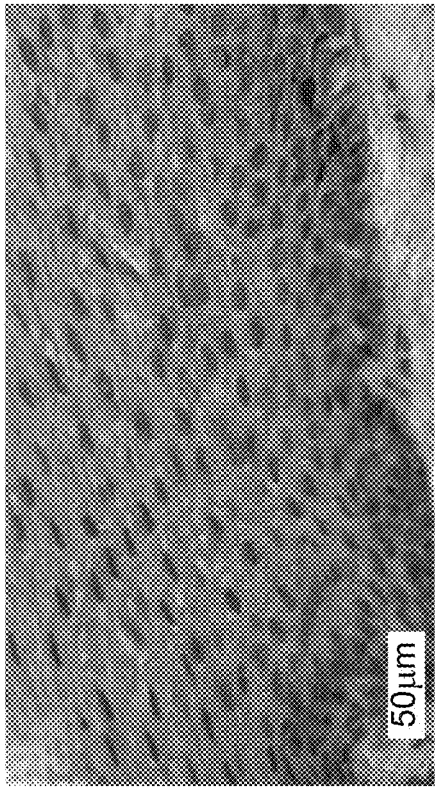
FIG. 8C is a photomicrograph of hematoxylin-eosin-stained section depicting a lower ⅓$^{rd}$ portion of epithelium at 48 hours (40×) in 6.6% propolis according to certain embodiments.
Figure 8D:
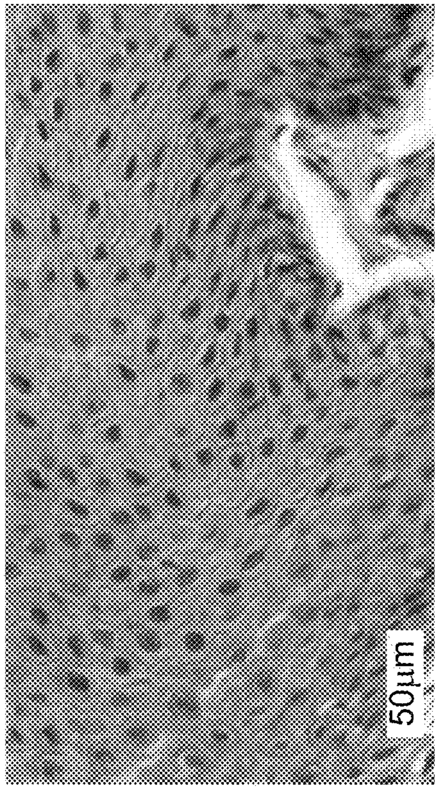
FIG. 8D is a photomicrograph of the hematoxylin-eosin-stained section depicting a lower ⅓$^{rd}$ portion of epithelium at 48 h (40×) in 6.6% propolis followed by 10% formalin, according to certain embodiments.

Referring to FIGS. 8A to 8D, photomicrographs of hematoxylin-eosin-stained section depicting a lower ⅓rd portion of epithelium in saline, formalin, a propolis-containing composition, and a mixture of the propolis-containing composition and formalin. In some embodiments, the tissue sample treated with saline shows autolysis, including but is not limited to cellular swelling (cytoplasmic vacuolization, shrinkage of the nucleus (pyknotic), indistinct cell borders, and poor staining quality, as depicted in FIG. 8A. As used herein the term "autolysis," "self-digestion," or "autodigestion" generally refers a process of self-digestion that occurs in cells and tissues after they die or are damaged. This digestion of cellular components occurs when the lysosomes within cells release their digestive enzymes, which then break down the cellular components and structures. In some further embodiments, at least 30% cells in the tissue sample show autolysis based on a total number of cells in the tissue sample before treatment, preferably at least 60%, or even more preferably at least 90% of the cells in the tissue sample treated with saline show autolysis. In some preferred embodiments, no more than 50%, preferably no more than 40%, or even more preferably no more than 30% of the cells in the tissue sample treated with formalin show autolysis based on the total total number of cells in the tissue sample before treatment, as depicted in FIG. 8B. In some more preferred embodiments, no more than 30%, preferably no more than 20%, or even more preferably no more than 10% of the cells in the tissue sample treated with the propolis-containing composition show autolysis based on the total number of cells in the tissue sample before treatment, as depicted in FIG. 8C. In some most preferred embodiments, no more than 30%, preferably no more than 20%, or even more preferably no more than 10% of the cells in the tissue sample treated with mixture of the propolis-containing composition and formalin show autolysis based on the total total number of cells in the tissue sample before treatment, as depicted in FIG. 8D. Other ranges are also possible.

In some embodiments, the propolis-containing composition may be used along with other tissue fixative compositions that are conventionally known in the art.

In another exemplary embodiment, a method of preparing the propolis-containing composition is described, according to certain embodiments. The order of the steps in which the method is described is not intended to be construed as a limitation, and any number of the described method steps can be combined in any order to implement the method. Additionally, individual steps may be removed or skipped from the method without departing from the spirit and scope of the present disclosure.

The method of preparing the propolis-containing composition includes mixing a propolis extract and at least one liquid containing propylene glycol and vegetable glycerol. In some embodiments, the mixing is performed for at least 10 minutes, preferably 10-600 minutes, 60-300 minutes, or about 120 minutes. Other ranges are also possible.

In some further embodiments, the method of preparing the propolis-containing composition optionally includes diluting the propolis-containing composition with at least double a volume of the total mixture, preferably 2 times, 3 times, 4 times, 5 times, 6 times, 7 times, 8 times, 9 times, 10 times, 20 times, 30 times, 40 times, or 50 times the volume of the total mixture, with deionized water to form a diluted solution. As used herein, the term 'deionized water' refers to water having most of the ions removed. The method of preparing the propolis-containing composition further optionally includes filtering the diluted solution. In an embodiment, the filtering is to remove any insoluble particulates from the solution greater than 10 μm in size. In an embodiment, the solution is filtered through a filter paper.

The fixed tissue shows enhanced preservation and fixation ability compared to a tissue sample treated with formalin. The tissue sample is treated with a fixative solution under conditions that allow the chemical molecules of the fixative agent in the fixative solution to diffuse throughout substantially the entire cross section of the sample. As used herein, the term "diffuse," or "diffusion" generally refers to a process by which molecules move from an area of high concentration to an area of low concentration. In the present disclosure, molecules of the propolis extract in the fixative solution move through the spaces or pores present in the solid tissue sample upon contact. In some embodiment, the molecules of the propolis extract may be absorbed or adhere to the surface of the tissue sample. In some further embodiments, the molecules of the propolis extract move thorough the spaces or pores present in the solid tissue sample, collide and adhere to the inner part of the tissue sample. This step is conducted using a volume of fixative for a period of time that allows for complete tissue infusion/diffusion. In some embodiments, the tissue sample is treated with a desired volume of the propolis-containing composition. The desired volume of the propolis-containing composition may be defined based on a volume of the sample tissue. In some embodiments, a ratio of the volume of the tissue sample to the volume of the propolis-containing composition is in a range of 1:1 to 1:20, preferably 1:5 to 1:15, or even more preferably about 1:10. Other ranges are also possible. In an embodiment, less volume of the propolis-containing composition is required to fix a tissue sample than formalin under the same conditions. In an embodiment, a lower volume of the propolis-containing composition is preferable to save costs. Upon selecting the desired volume of the propolis-containing composition based on the volume of the tissue sample, the tissue sample is treated with the propolis-containing composition for a desired duration. In one embodiment, the tissue sample is treated with the propolis-containing composition solution for 1-72 hours, preferably 5-60 hours, 10-50 hours, 15-40 hours, or 20-30 hours. In one embodiment, the tissue sample is treated with the propolis-containing composition for 1-24 hours. In another embodiment, the tissue sample is treated with the propolis-containing composition for 1-12 hours. In an embodiment, less time is required to fix a tissue sample when using the propolis-containing composition than when using formalin under the same conditions. In an embodiment, a lower fixation time is preferable as to save costs and receive rapid results. In some embodiments, the tissue is fixed with the propolis-containing composition at an elevated temperature of 20-40° C., preferably 25-35° C. or approximately 30° C. Other ranges are also possible.

In an embodiment, no bacterial growth is observed in the fixed tissue sample after 24 hours, preferably 36 hours, 48 hours, or 72 hours. In an embodiment, less than 10% of the surface area of the fixed tissue sample exhibits bacteria growth after 24 hours, preferably less than 5% or less than 1%. In an embodiment, the propolis-containing composition has antimicrobial properties.

The fixed tissue sample is further stained with at least one stain selected from the group consisting of a hematoxylin and eosin stain, a reticulin stain, a trichrome stain, a periodic acid-schiff stain, a desmin stain, a thyroid transcription factor-1 (TTF1) stain, a cluster of differentiation 3 (CD3) stain, and a paired-box gene 8 (PAX8) stain. As used herein, the term 'staining' refers to a method of imparting color to cells, tissues or microscopic components, so the cells are highlighted and visualized better under a microscope. In an embodiment, the stain is any stain known in the art.

Hematoxylin and eosin stain is the most common stain used in histology for medical diagnosis. It is the combination of two histological stains: hematoxylin and eosin. The hematoxylin stains cell nuclei a purplish blue, and eosin stains the extracellular matrix and cytoplasm pink, with other structures taking on different shades, hues, and combinations of these colors. Pathologists can thereby differentiate between the nuclear and cytoplasmic parts of a cell, and additionally, the overall patterns of coloration from the stain show the general layout and distribution of cells and provides a general overview of a tissue sample's structure.

Special stains include but are not limited to reticulin stain, trichrome stain, periodic acid-schiff stain. Special stains employ a dye or chemical which has an affinity for a particular tissue component. For example, Massons trichrome stain helps to highlight the supporting collagenous stroma in sections from a variety of organs. This helps to determine a pattern of tissue injury. Trichrome will also aid in identifying normal structures, such as connective tissue capsules of organs, the lamina propria of the gastrointestinal tract, and the bronchovascular structures in the lung. Another example includes a reticulin stain which is useful in parenchymal organs such as liver and spleen to outline the architecture. Delicate reticular fibers, which are argyrophilic, can be seen. A reticulin stain occasionally helps to highlight the growth pattern of neoplasms.

Immunohistochemical staining is accomplished with antibodies that recognize the target antigen. Immunohistochemical stains include but are not limited to desmin stain, TTF-1 stain, CD3 stain, and PAX8 stain. For example, the PAX8 stain targets PAX8 and helps to visualize the presence of PAX8 in a tissue to potentially diagnose certain cancers. Antigen retrieval steps may be required with immunohistochemical staining. Tissues that have been preserved with formaldehyde or formalin contain a variety of chemical modifications that can reduce the detectability of proteins in biomedical procedures. An antigen retrieval method is typically used to reduce these chemical modifications and improve image quality of immunohistochemical stained tissues. In an embodiment, a tissue sample fixed with the propolis-containing composition does not require an antigen retrieval step prior to staining with an immunohistochemical stain.

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

In an embodiment, the fixed tissue sample is submerged in a solution of the stain. In an embodiment, a fixed tissue sample fixed with the propolis-containing composition is compatible with a hematoxylin and eosin stain, a reticulin stain, a trichrome stain, a periodic acid-schiff stain, a desmin stain, a thyroid transcription factor-1 (TTF-1) stain, a cluster of differentiation 3 (CD3) stain, and a Paired-box gene 8 (PAX8 stain).

Figure 2:
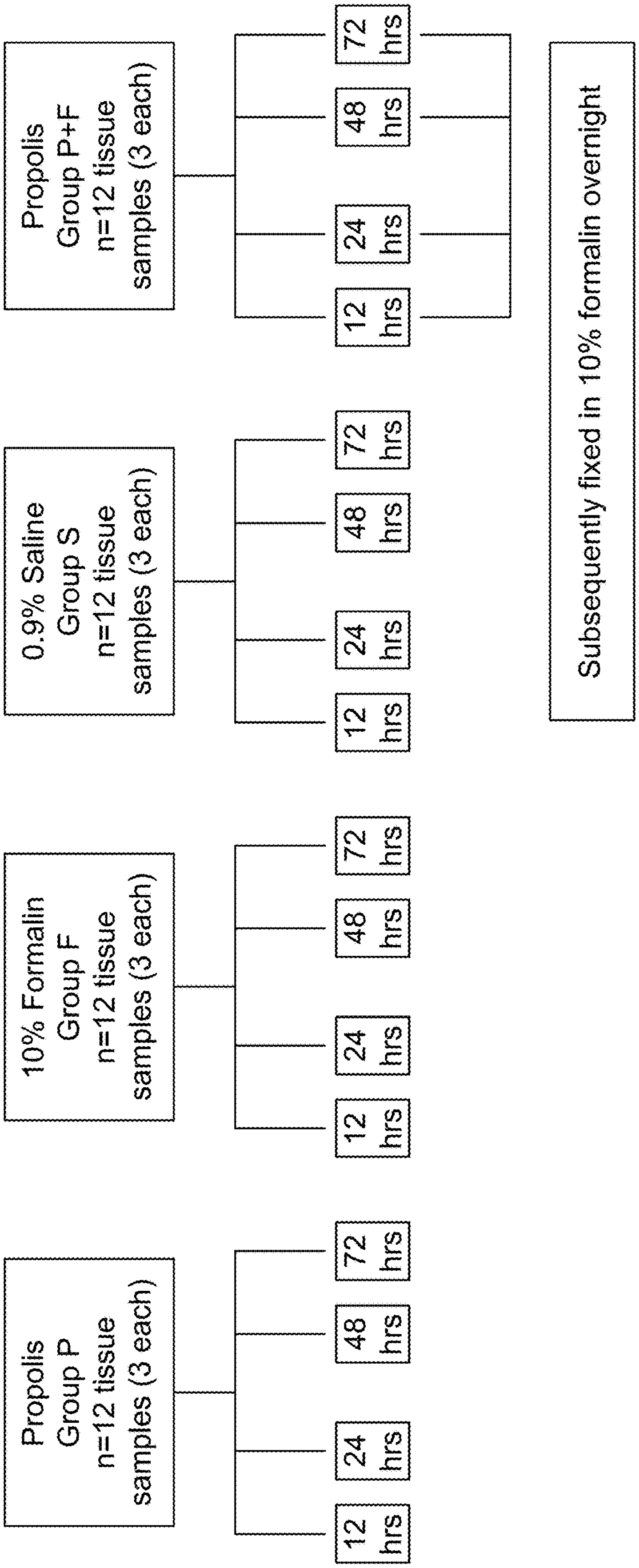
FIG. 2 is a schematic flow diagram depicting a process of specimen preparation, according to certain embodiments.
Figure 3A:
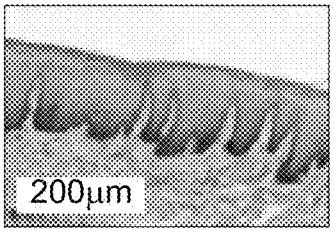
FIG. 3A-FIG. 3D show photomicrographs of hematoxylin-eosin-stained sections of tissues fixed in 0.9% saline (group S) at 12 hours, 24 hours, 48 hours, and 72 hours, respectively, at 5× magnification, according to certain embodiments.
Figure 3B:
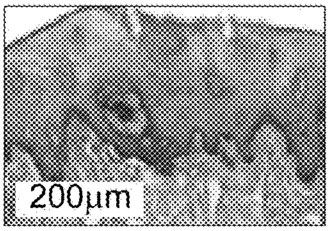
Figure 3C:
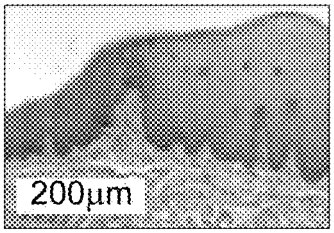
Figure 3D:
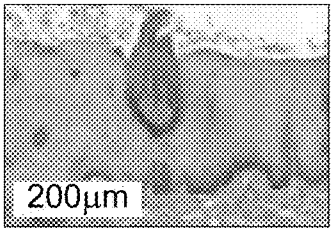
Figure 3E:
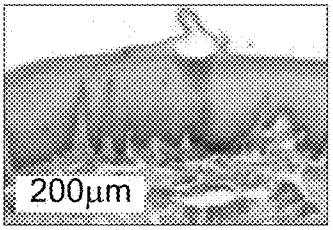
FIG. 3E-FIG. 3H show photomicrographs of hematoxylin-eosin-stained sections of tissues fixed in 10% formalin (group F) at 12 hours, 24 hours, 48 hours, and 72 hours, respectively, at 5× magnification, according to certain embodiments.
Figure 3F:
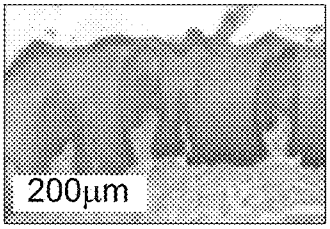
Figure 3G:
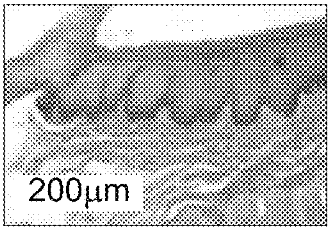
Figure 3H:
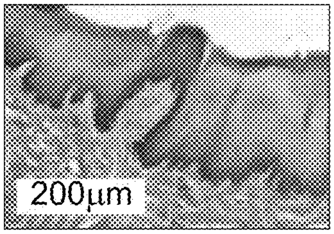
Figure 3I:
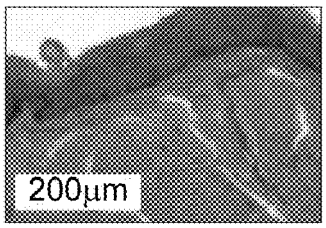
FIG. 3I-FIG. 3L show photomicrographs of hematoxylin-eosin-stained sections of tissues fixed in 6.6% propolis (group P) at 12 hours, 24 hours, 48 hours, and 72 hours, respectively, at 5× magnification, according to certain embodiments.
Figure 3J:
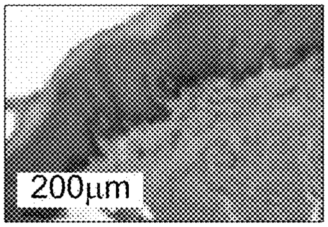
Figure 3K:
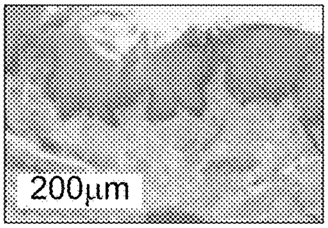
Figure 3L:
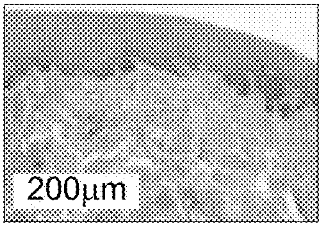
Figure 3M:
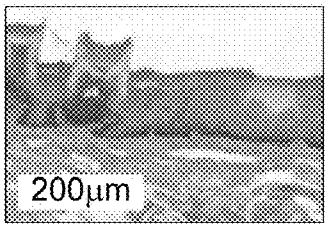
FIG. 3M-FIG. 3P show photomicrographs of hematoxylin-eosin-stained sections of tissues fixed in 6.6% propolis and 10% formalin (group P+F) at 12 hours, 24 hours, 48 hours, and 72 hours, respectively, at 5× magnification, according to certain embodiments.
Figure 3N:
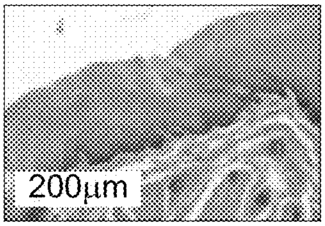
Figure 3O:
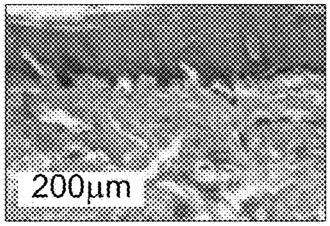
Figure 3P:
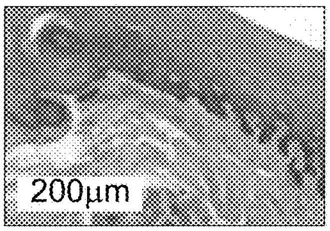
Figure 4A:
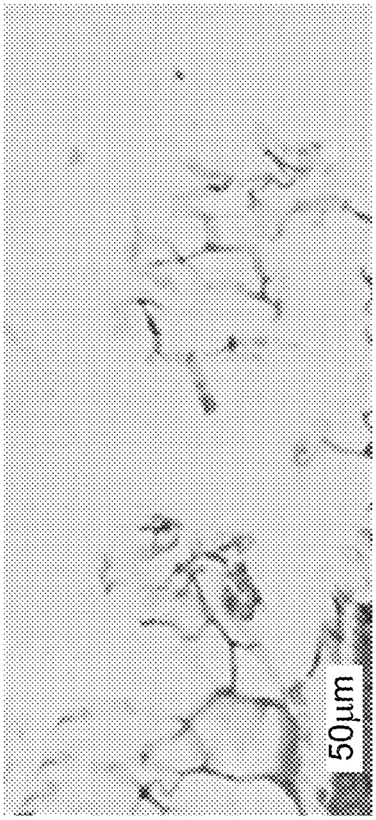
FIG. 4A shows a photomicrograph of a hematoxylin-eosin-stained section of adipose tissue showing a scoring system, with score 1 indicating a loss of cell wall integrity in most adipocytes, according to certain embodiments.
Figure 4B:
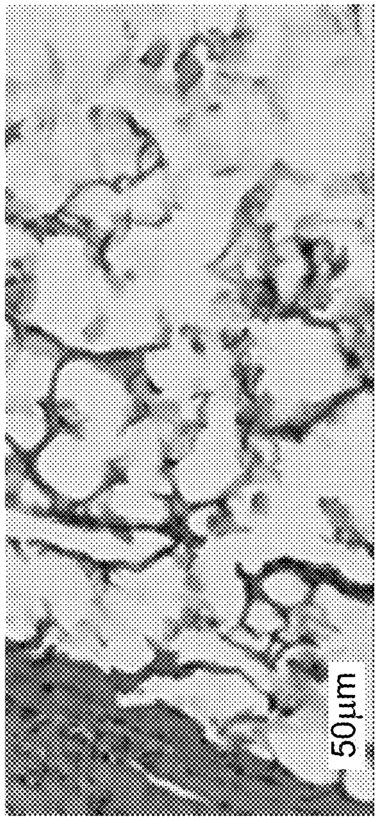
FIG. 4B shows a photomicrograph of a hematoxylin-eosin-stained section of adipose tissue showing a scoring system, with score 2 indicating a shredded cell wall with minimal preservation of cell wall of some adipocytes, according to certain embodiments.
Figure 4C:
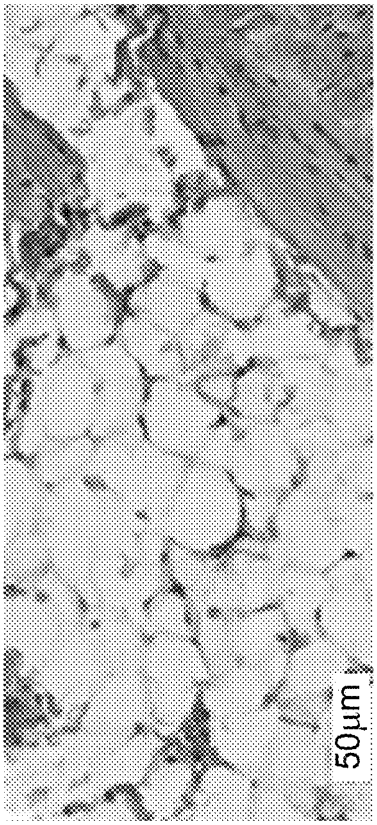
FIG. 4C shows a photomicrograph of a hematoxylin-eosin-stained section of adipose tissue showing a scoring system, with a score of 3 indicating fair preservation of the cell wall of adipocytes, according to certain embodiments.
Figure 4D:
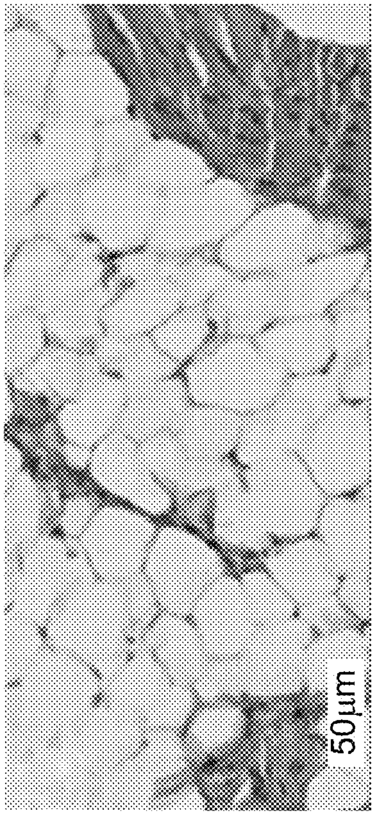
FIG. 4D shows a photomicrograph of a hematoxylin-eosin-stained section of adipose tissue showing a scoring system, with a score of 4 indicating normal preservation of adipocytes (20×), according to certain embodiments.
Figure 6:
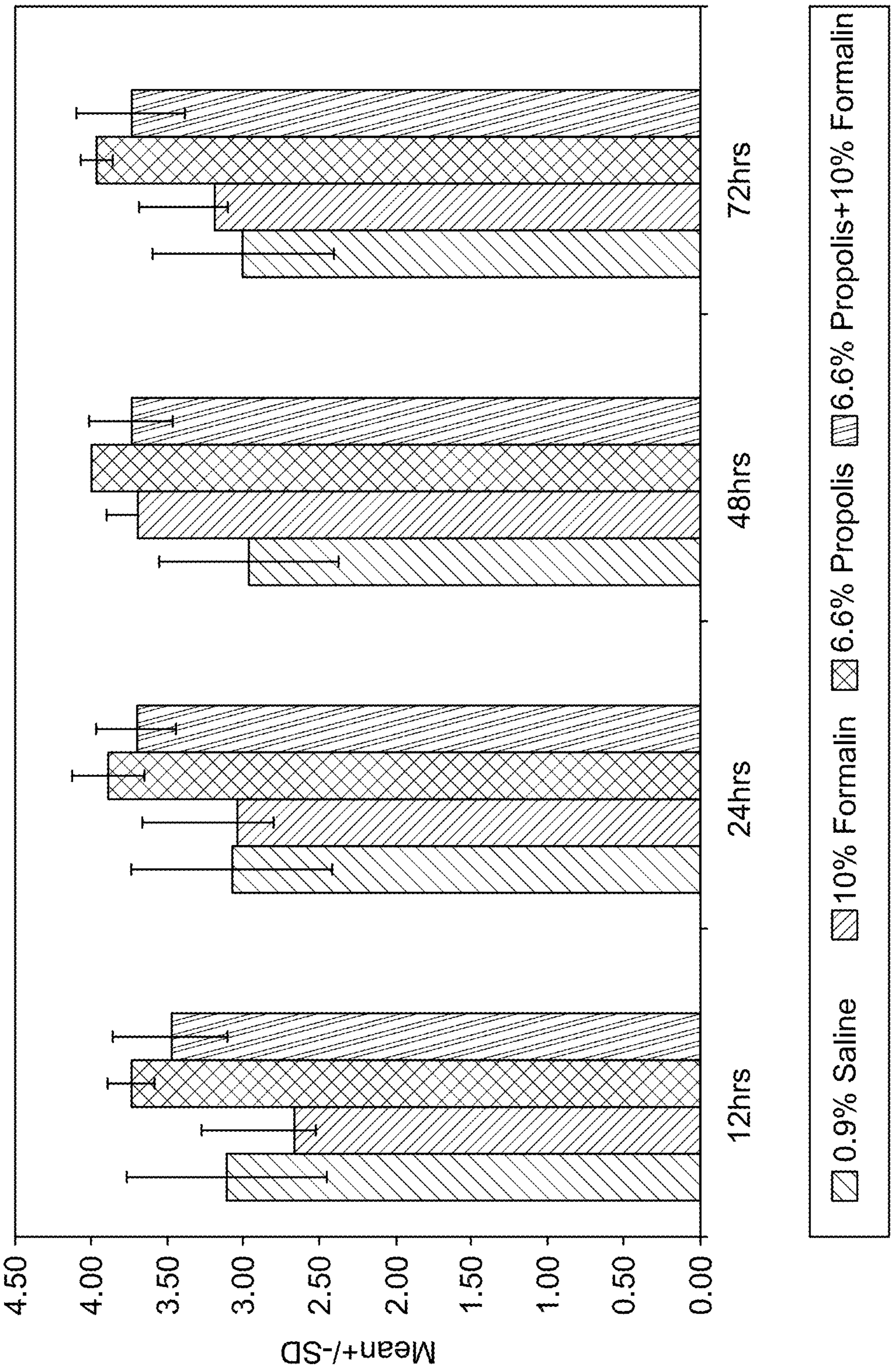
FIG. 6 is a graph showing between-group comparisons at different time points, according to certain embodiments.
Figure 7:
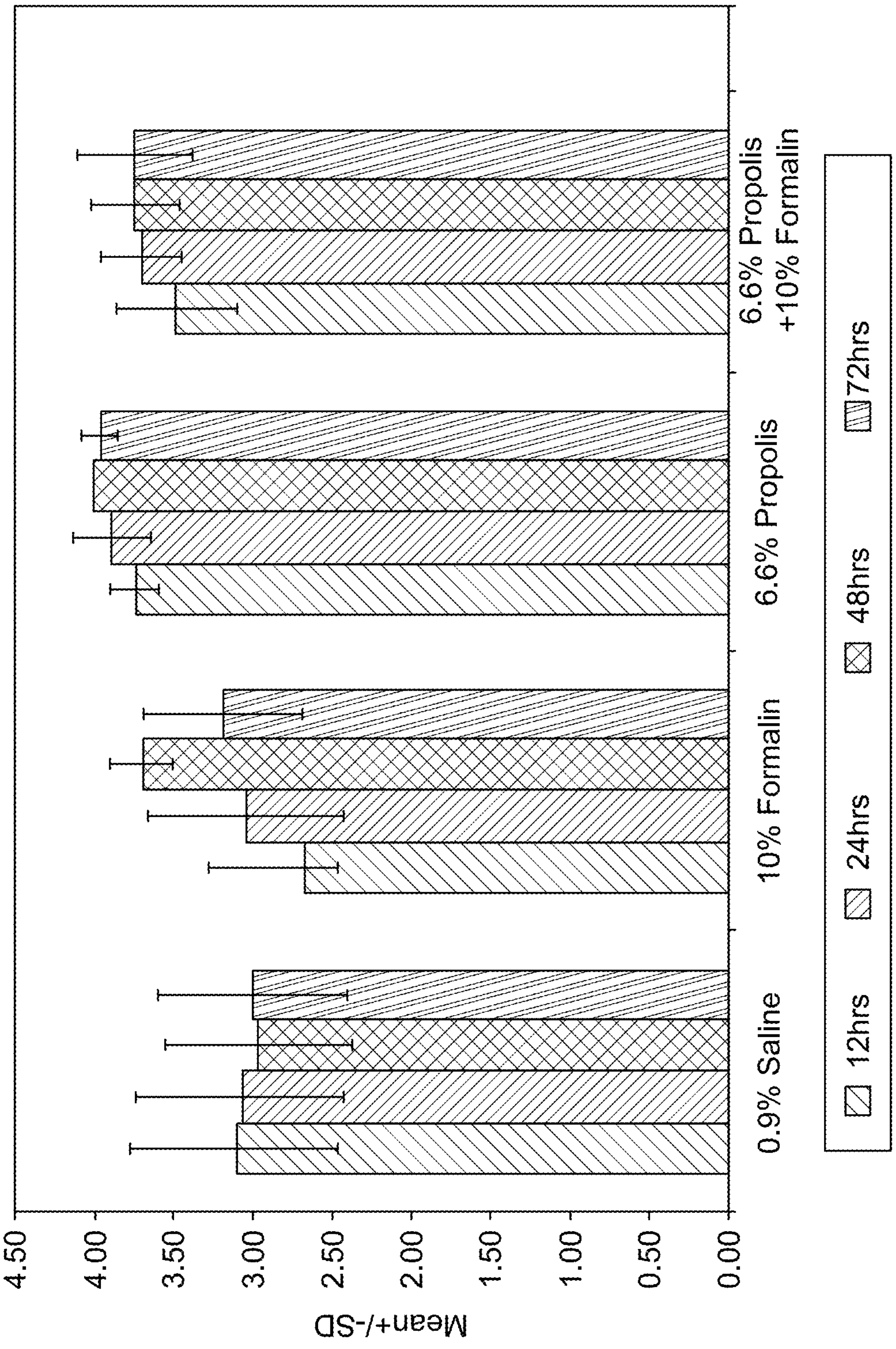
FIG. 7 is a graph showing within-group comparison at different time points, according to certain embodiments.

Aspects of the present disclosure are directed to a method of fixing a tissue sample using a propolis-containing composition. The effectiveness of propolis to 10% formalin was compared as a natural fixative solution. To evaluate the effectiveness of the propolis-containing composition as a fixative agent, tissue specimens were collected from goats' tongues and immediately placed in (1) about 6.6% propolis, (2) about 10% natural buffered formalin (positive control), (3) about 6.6% propolis followed by about 10% formalin, and (4) about 0.9% saline (negative control), as depicted in FIG. 2. The tissue samples were fixed at different time points (12, 24, 48, and 72 h) at room temperature, followed by processing and staining, as depicted in FIGS. 3A to 3P. The quality of the microscopic parameters was blindly assessed by two oral and maxillofacial pathologists using a numerical scoring scale. The scores were statistically analyzed, as depicted in FIGS. 6 and 7, indicating that the fixation of tissue samples placed in 6.6% propolis was statistically better than that of samples placed in 10% formalin and 0.9% saline at different time points.

EXAMPLES

The following examples demonstrate a method of fixing a tissue sample, as described herein. The examples are provided solely for illustration and are not to be construed as limitations of the present disclosure, as many variations thereof are possible without departing from the spirit and scope of the present disclosure.

Example 1: Materials

This experimental in vitro study used biopsy specimens collected from goats' tongues. The study was approved by Imam Abdulrahman bin Faisal University Institutional Review Board (IRB-2021-02-468).

Example 2: Tissue Samples Preparation

Figure 1B:
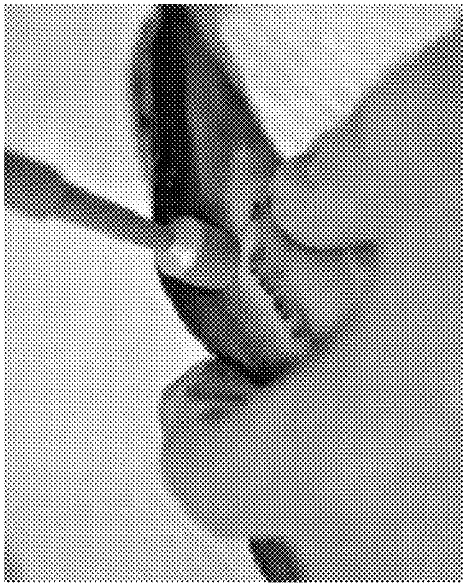
FIG. 1B-FIG. 1C show the images of tissue samples through punch biopsy, according to certain embodiments.
Figure 1C:
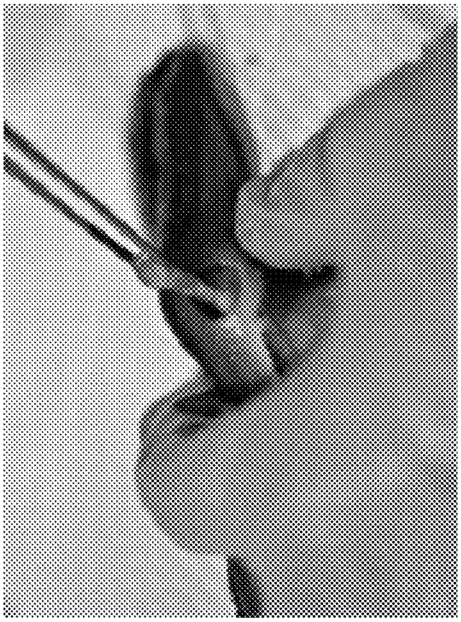
Figure 1D:
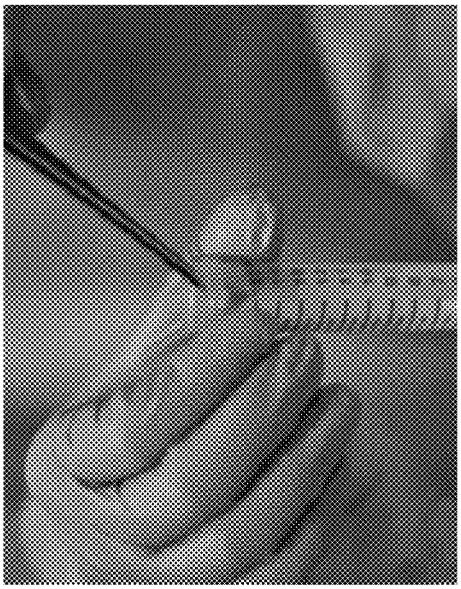
FIG. 1D shows the image of the tissue samples placed directly in a 15 milliliters (mL) tube containing a fixative solution, according to certain embodiments.

FIG. 1A shows an image of the tongues of ten recently slaughtered goats collected from a local slaughterhouse. The interval between the time of slaughter and tongue biopsy was consistently between 20 and 30 min. A total of 48 biopsy samples were obtained from the lateral surfaces of the tongues using an 8-millimeter (mm) diameter punch biopsy (FIG. 1B-FIG. 1C). FIG. 1D shows three samples were directly placed in three different 15 milliliters (mL) tubes into the following solutions: (a) 6.6% propolis extract (Nature's Answer, alcohol-free, 2000 mg/30 mL; Group P), (b) 10% buffered formalin (positive control; Group F), (c) 0.9% normal saline (Pharmaceutical Solutions Industry, 0.9% w/v sodium chloride; negative control; Group S), and (d) 6.6% propolis and then subsequently transferred to 10% formalin for overnight (Group P+F). According to the manufacturer, the liquid contains 2 grams (g) of propolis extract. Hence, the concentration of propolis was established according to the following formula: weight (w)/volume (v) %=weight of the solute/volume of solution×100. (w/v %=2/30×100, which is 6.66%.). FIG. 2 illustrates the flowchart of specimen preparation. Each group was fixed in their solution at room temperature (20-25° C.) for different time points (12, 24, 48, and 72 h). Only Group P+F was transferred to 10% buffered formalin overnight (FIG. 2).

Example 3: Preparation of Histological Slides

All tissues were dehydrated by immersing them in a series of alcohol solutions of increasing concentrations. Then, tissues were cleared using a clearing reagent, xylene. To prepare the tissue block, the tissues were oriented and embedded into melted paraffin wax at a high temperature. Finally, the embedded paraffin tissue blocks were cut into slice sections using a microtome and stained with hematoxylin and eosin.

Example 4: Histological Assessment

FIGS. 3A-3P shows the prepared slides, which were scanned into a virtual format, and the quality of various histological structures was blindly evaluated by two calibrated oral and maxillofacial pathologists individually. The following microscopic structures were assessed: (1) the superficial ⅓rd of the epithelium, (2) the middle ⅓rd of the epithelium, (3) the lower ⅓rd of the epithelium, (4) basement membrane and rete ridges, (5) fibrous connective tissue, (6) blood vessels and endothelial cells, (7) skeletal muscles, (8) adipose tissue, and (9) nerve bundles.

To standardize the assessment methods and minimize the subjectivity between the two pathologists, a numerical scoring scale was created to evaluate different microscopic structures, and the scores were classified from 1 to 4, as follows: (1) major changes that affect the diagnosis, (2) minor changes that may affect diagnosis, (3) minor changes that do not affect diagnosis, and (4) no apparent change (Table 1). FIG. 4A-FIG. 4D show photomicrographs of adipocytes of different biopsy tissue samples placed in various solutions showing different scores according to the numerical scoring scale.

TABLE 1

Numerical scale for microscopic tissue structures assessment.

| Score | Histological Criteria |
|---|---|
| 4 (FIG. 4D) | No apparent change |
| 3 (FIG. 4C) | Minor changes that do not affect the diagnosis |
| 2 (FIG. 4B) | Minor changes that may affect the diagnosis |
| 1 (FIG. 4A) | Significant changes that affect the diagnosis |

Example 5: Statistical Analysis

Kappa statistics were used to determine the variability between the two different examiners. An analysis of variance (ANOVA) was performed to compare the mean scores from various media, followed by Tukey's multiple post hoc analysis. SPSS Statistics version 27 was used for all statistical analyses.

Example 6: Results

Figure 5:
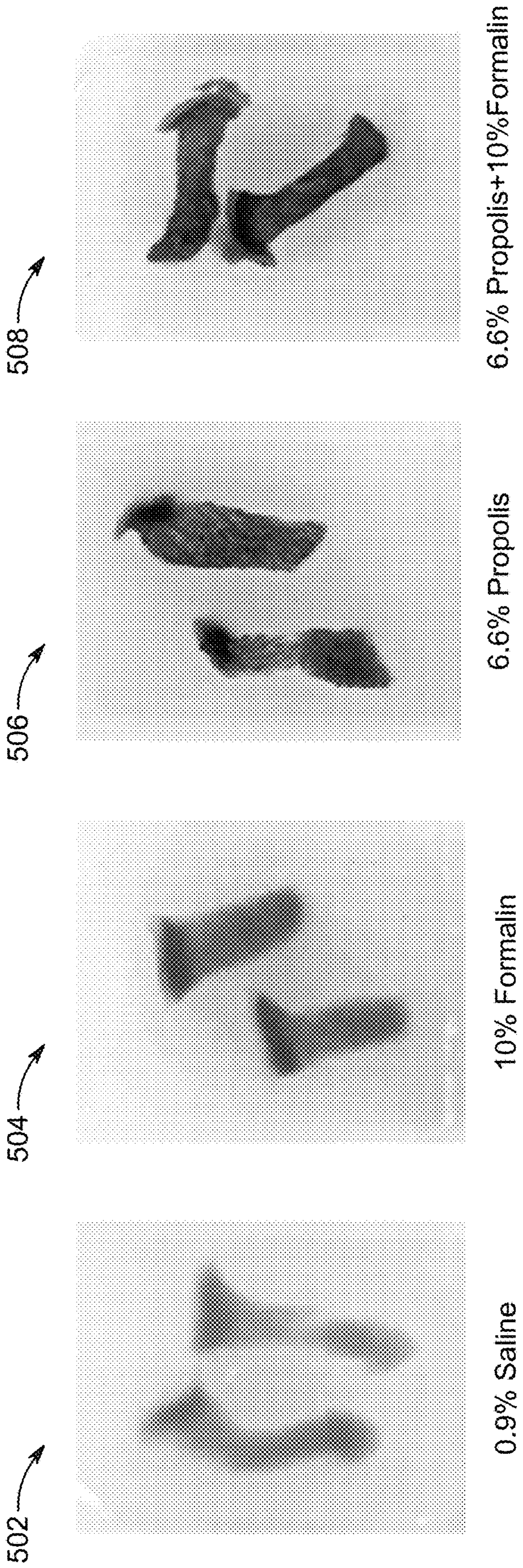
FIG. 5 shows paraffin wax-embedded blocks showing discoloration in tissues placed in 6.6% propolis (506) compared with those placed in other solutions, namely, 0.9% saline (502), 10% formalin (504), and a combination of 6.6% propolis and 10% formalin (508), according to certain embodiments.

Tissues placed in the 6.6% propolis became firmer over time during grossing and sectioning than those placed in other solutions. Furthermore, FIG. 5 shows the tissues placed either in 6.6% propolis only (Group P) or 6.6% propolis followed by 10% formalin (Group P+F) exhibited a dark brown color compared with those placed in 0.9% saline and 10% formalin.

According to Landis and Koch agreement measures for categorical data, the Kappa statistics in this study revealed substantial agreement (kappa=0.81) between the two oral pathologists in the scores of tissues placed in propolis (Group P), while the scores in other groups demonstrated a moderate agreement between the examiners as shown in Table 2 [Landis, J. R.; Koch, G. G. The measurement of observer agreement for categorical data. Biometrics 1977, 33, 159-174, which is incorporated herein by reference in its entirety].

TABLE 2

Kappa statistics for inter-oral pathologists' agreement.

| Fixative Agents | Agreement | Kappa | Strength of Agreement |
|---|---|---|---|
| 0.9% saline | 83.33% | 0.47 | Moderate |
| 10% formalin | 77.78% | 0.55 | Moderate |
| 6.6% propolis | 88.89% | 0.61 | Substantial |
| 6.6% propolis + 10% formalin | 77.78% | 0.57 | Moderate |

Comparison between different groups at different time points

Group P tissue samples had the highest mean scores at all time points, followed by Group P+F tissue samples.

Example 7: Twelve Hours

Group P tissue samples demonstrated the highest mean score (mean=3.74), followed by Group P+F tissue samples (mean=3.48) (Table 3).

TABLE 3

Comparison of the fixative ability of different solutions at different treatment times.

| | 12 hours | | 24 hours | | 48 hours | | 72 hours | |
|---|---|---|---|---|---|---|---|---|
| Solution | Mean | SD § | Mean | SD | Mean | SD | Mean | SD |
| 0.9% Saline | 3.11 | 0.65 | 3.07 | 0.66 | 2.96 | 0.59 | 3.00 | 0.60 |
| 10% Formalin | 2.67 | 0.60 | 3.04 | 0.63 | 3.70 | 0.20 | 3.19 | 0.50 |
| 6.6% Propolis | 3.74 | 0.15 | 3.89 | 0.24 | 4.00 | 0.00 | 3.96 | 0.11 |
| 6.6% Propolis + 10% Formalin | 3.48 | 0.38 | 3.70 | 0.26 | 3.74 | 0.28 | 3.74 | 0.36 |

Pairwise comparisons by Tukey's multiple post hoc procedures

| | 12 hours | 24 hours | 48 hours | 72 hours |
|---|---|---|---|---|
| 6.6% Saline vs. 10% Formalin | p = 0.3702 | p = 0.9999 | p = 0.0006 | p = 0.9037 |
| 0.9% Saline vs. 6.6% Propolis | p = 0.0905 | p = 0.0129 * | p = 0.0001 | p = 0.0006 * |
| 0.9% Saline vs. 6.6% Propolis + 10% Formalin | p = 0.5518 | p = 0.0852 | p = 0.0004 | p = 0.0096 * |
| 10% Formalin vs. 6.6% Propolis | p = 0.0008 * | p = 0.0086 * | p = 0.3814 | p = 0.0059 * |
| 10% Formalin vs. 6.6% Propolis + 10% Formalin | p = 0.0142 * | p = 0.0602 | p = 0.9994 | p = 0.0837 |
| 6.6% Propolis vs. 6.6% Propolis + 10% Formalin | p = 0.8213 | p = 0.9374 | p = 0.5153 | p = 0.8293 |

* Indicates statistical significance.

§ SD: Standard deviation.

In the between-group analysis, Group P tissue samples demonstrated a statistically significantly higher mean score than Group F tissue samples (p=0.0008). Similarly, Group P+F tissue samples had a statistically significantly higher mean score than Group F tissue samples (p=0.0142) (Table 3).

Example 8: Twenty-Four Hours

Group P tissue samples demonstrated the highest mean score (mean=3.89), followed by Group P+F tissue samples (mean=3.70) (Table 3). When comparing the mean scores for all solutions, it was found that keeping the tissue samples in 6.6% propolis (Group P) for 24 hours enhanced the tissue fixation and showed better quality of various microscopic structures than those placed in 10% formalin (Group F) and 0.9% saline (Group S) (p=0.0086 and p=0.0129, respectively) (Table 3).

Example 9: Forty-Eight Hours

Group P tissue samples demonstrated an excellent quality of various microscopic parameters with the highest mean score (mean=4.00), followed by Group P+F tissue samples (mean=3.74) (Table 3). However, when comparing the mean scores obtained for various solutions, we found that tissues placed in 0.9% saline (Group S) for 48 hours demonstrated a substandard quality of different microscopic structures, with a statistically significantly lower mean score than those placed in 6.6% propolis (Group P), 6.6% propolis followed by 10% formalin (Group P+F), and 10% formalin (Group F) (p=0.0001, p=0.0004, and p=0.0006, respectively) (Table 3).

Example 10: Seventy-Two Hours

Group P tissue samples had the highest mean score (mean=3.96), followed by Group P+F tissue samples (mean=3.74) (Table 3). In addition, group P tissue samples scored statistically significantly higher mean scores than Group S and Group F tissue samples (p=0.0006 and p=0.0059, respectively). Similarly, Group P+F tissue samples had a statistically significant higher mean score than Group S tissue samples (p=0.0096) (Table 3). FIG. 6 provides a graph showing a comparison between groups. Group P tissue samples demonstrated the highest score in the study, followed by Group P+F tissue samples.

Changes in the mean score at different points compared to 12 hours.

Changes from 12 to 24 Hours

Between-Group Comparison

When all the mean scores of various solutions were compared from 12 to 24 hours, a statistically non-significant improvement in the fixative ability of 10% formalin (Group F), propolis (Group P), and propolis, followed by 10% formalin (Group P+F) was observed at 24 hours compared with 12 hours; while Group S tissue samples showed a statistically non-significant decrease in the mean score (Table 4).

TABLE 4

Comparison of the fixative ability of different solutions with change in scores from 12 hours to 24, 48, and 72-hour treatment times

| | Changes from 12 h to | | | | | |
|---|---|---|---|---|---|---|
| | 24 hours | | 48 hours | | 72 hours | |
| Solution | Mean | SD § | Mean | SD | Mean | SD |
| 0.9% Saline | 0.04 | 0.45 | 0.15 | 0.38 | 0.11 | 0.53 |
| 10% Formalin | −0.37 | 0.39 | −1.04 | 0.51 | −0.52 | 0.34 |
| 6.6% Propolis | −0.15 | 0.24 | −0.26 | 0.15 | −0.22 | 0.17 |
| 6.6% Propolis + 10% Formalin | −0.22 | 0.24 | −0.26 | 0.28 | −0.26 | 0.22 |
| Pairwise comparisons by Tukey's multiple post hoc procedures | | | | | | |
| 0.9% Saline vs. 10% Formalin | p = 0.1569 | | p = 0.0001 * | | p = 0.0152 * | |
| 0.9% Saline vs. 6.6% Propolis | p = 0.8262 | | p = 0.2024 | | p = 0.4077 | |
| 0.9% Saline vs. 6.6% Propolis + 10% Formalin | p = 0.5797 | | p = 0.2024 | | p = 0.3033 | |
| 10% Formalin vs. 6.6% Propolis | p = 0.7104 | | p = 0.0014 * | | p = 0.5254 | |
| 10% Formalin vs. 6.6% Propolis + 10% Formalin | p = 0.9142 | | p = 0.0014 | | p = 0.6482 | |
| 6.6% Propolis vs. 6.6% Propolis + 10% Formalin | p = 0.9931 | | p = 1.0000 | | p = 0.9997 | |

* Indicates statistical significance.

§ SD: Standard deviation.

Within-Group Comparison

Storing the tissue samples for more than 12 hours in 10% formalin (Group F) and propolis followed by 10% formalin (Group P+F) showed statistically significant improvements in tissue fixation compared with tissues fixed only for 12 hours (0.0212 and 0.0222, respectively) (Table 5).

TABLE 5

Within-group comparisons at different time points for each solution by ANOVA. Changes from 12 to 48 hours

| Solution | Change (time) | Mean Diff. ‡ | SD Diff. † | Changes (%) | p-Value |
|---|---|---|---|---|---|
| 0.9% Saline | 12 to 24 h | 0.04 | 0.45 | 1.19 | 0.8131 |
| | 12 to 48 h | 0.15 | 0.38 | 4.76 | 0.2721 |
| | 12 to 72 h | 0.11 | 0.53 | 3.57 | 0.5447 |
| 10% Formalin | 12 to 24 h | −0.37 | 0.39 | −13.89 | 0.0212* |
| | 12 to 48 h | −1.04 | 0.51 | −38.89 | 0.0003* |
| | 12 to 72 h | −0.52 | 0.34 | −19.44 | 0.0017* |
| 6.6% Propolis | 12 to 24 h | −0.15 | 0.24 | −3.96 | 0.1038 |
| | 12 to 48 h | −0.26 | 0.15 | −6.93 | 0.0007* |
| | 12 to 72 h | −0.22 | 0.17 | −5.94 | 0.0039* |
| 6.6% Propolis + | 12 to 24 h | −0.22 | 0.24 | −6.38 | 0.0222* |
| 10% Formalin | 12 to 48 h | −0.26 | 0.28 | −7.45 | 0.0232* |
| | 12 to 72 h | −0.26 | 0.22 | −7.45 | 0.0081* |

* Indicates statistical significance.

‡ Mean Diff.: Difference between mean scores of a solution at 2 different time points.

† SD Diff.: Difference between standard deviations of a solution at 2 different time points.

Between-Group Comparison

When various solutions were compared, 6.6% propolis (Group P) and 6.6% propolis followed by 10% formalin (Group P+S) showed statistically significant improvements in tissue fixation compared with 10% formalin (Group F) (p=0.0014, both groups). Similarly, Group F tissue samples showed a statistically significant improvement in fixation ability compared with Group S tissue samples (p=0.0001) (Table 4).

Within-Group Comparison

Keeping the tissue samples in 6.6% propolis (Group P), 10% formalin (Group F), and propolis followed by 10% formalin (Group P+F) for 48 h showed persistent improvement in their fixation ability compared with keeping them for 12 hours (p=0.0007, p=0.0003, and p=0.0232) (Table 5).

Changes from 12 to 72 Hours

Between-Group Comparison

Almost all groups showed improvement in the mean score of various microscopic parameters at 72 hours compared with 12 hours, except Group S. However, this improvement decreased compared to the mean score at 24 and 48 hours. A statistically significant improvement in tissue fixation was observed in Group F tissue samples compared with Group S tissue samples (p=0.0152) (Table 4).

Within-Group Comparison

A statistically significant improvement in the mean scores of various microscopic parameters was observed in Group F, Group P, and Group P+F compared with 12 hours (p=0.0017, p=0.0039, and p=0.0081, respectively) (Table 5). FIG. 7 provides a graph showing that most tissue samples in various solutions scored a maximum at around 48 hours, except Group S tissue samples, which had a top score at 24 hours.

Comparison of Fixation Ability of Different Solutions Through Various Microscopic Structures There was no significant difference in the mean score of almost all the microscopic structures individually. However, tissue samples placed in 6.6% propolis (Group P) showed better quality in the superficial one-third of the epithelial lining with a significantly higher mean score compared to a tissue placed in 0.9% saline (p=0.03) (Table 6a-c).

TABLE 6

(a) Comparison of the fixative ability of different solutions in different microscopic structures (epithelium).

| | Epithelium | | | | | |
|---|---|---|---|---|---|---|
| | Superficial 1/3rd | | Middle 1/3rd | | Lower 1/3rd | |
| Solution | Mean | SD § | Mean | SD | Mean | SD |
| 0.9% Saline | 2.58 | 0.44 | 2.83 | 0.30 | 3.42 | 0.1 |
| 10% Formalin | 3.12 | 0.39 | 3.21 | 0.29 | 3.41 | 0.22 |
| 6.6% Propolis | 3.37 | 0.16 | 3.21 | 0.21 | 3.41 | 0.22 |
| 6.6% Propolis + 10% Formalin | 3.16 | 0.36 | 3.21 | 0.16 | 3.50 | 0.36 |
| Pairwise comparisons by Tukey's multiple post hoc procedures | | | | | | |
| 0.9% Saline vs. 10% Formalin | p = 0.2342 | | p = 0.4502 | | p = 1.0000 | |
| 0.9% Saline vs. 6.6% Propolis | p = 0.0388* | | p = 0.4502 | | p = 1.0000 | |
| 0.9% Saline vs. 6.6% Propolis + 10% Formalin | p = 0.1779 | | p = 0.4502 | | p = 0.9859 | |
| 10% Formalin vs. 6.6% Propolis | p = 0.8374 | | p = 1.0000 | | p = 1.0000 | |
| 10% Formalin vs. 6.6% Propolis + 10% Formalin | p = 0.9998 | | p = 1.0000 | | p = 0.9842 | |
| 6.6% Propolis vs. 6.6% Propolis + 10% Formalin | p = 0.9080 | | p = 1.0000 | | p = 0.9842 | |

TABLE 6

(b) Comparison of the fixative ability of different solutions in different microscopic structures (basement membrane, nerve bundles, and fibrous tissue)

| Solution | Basement Membrane Mean | Basement Membrane SD | Nerve Bundles Mean | Nerve Bundles SD | Fibrous Tissue Mean | Fibrous Tissue SD |
|---|---|---|---|---|---|---|
| 0.9% Saline | 3.62 | 0.16 | 3.66 | 0.13 | 2.83 | 0.2 |
| 10% Formalin | 3.7 | 0.09 | 3.66 | 0.24 | 2.92 | 0.59 |
| 6.6% Propolis | 3.58 | 0.21 | 3.71 | 0.29 | 3.25 | 0.10 |
| 6.6% Propolis + 10% Formalin | 3.87 | 0.09 | 3.54 | 0.21 | 3.16 | 0.24 |
| 0.9% Saline + 10% Formalin | 3.54 | 0.44 | 3.46 | 0.44 | 2.79 | 0.48 |
| Pairwise comparisons by Tukey's multiple post hoc procedures | | | | | | |
| 0.9% Saline vs. 10% Formalin | p = 0.9883 | | p = 1.0000 | | p = 0.9973 | |
| 0.9% Saline vs. 6.6% Propolis | p = 0.9990 | | p = 0.9995 | | p = 0.5225 | |
| 0.9% Saline vs. 6.6% Propolis + 10% Formalin | p = 0.5814 | | p = 0.9697 | | p = 0.7081 | |
| 10% Formalin vs. 6.6% Propolis | p = 0.9456 | | p = 0.9995 | | p = 0.7136 | |
| 10% Formalin vs. 6.6% Propolis + 10% Formalin | p = 0.8442 | | p = 0.9697 | | p = 0.8724 | |
| 6.6% Propolis vs. 6.6% Propolis + 10% Formalin | p = 0.4367 | | p = 0.9157 | | p = 0.9976 | |

TABLE 6

(c): Comparison of the fixative ability of different solutions in different microscopic structures (blood vessels, skeletal muscles, and adipose tissue).

| Solution | Blood Vessels Mean | Blood Vessels SD | Skeletal Muscles Mean | Skeletal Muscles SD | Adipose Tissue Mean | Adipose Tissue SD |
|---|---|---|---|---|---|---|
| 0.9% Saline | 3.71 | 0.29 | 3.04 | 0.29 | 3.29 | 0.25 |
| 10% Formalin | 3.79 | 0.16 | 2.75 | 0.4 | 3.29 | 0.34 |
| 6.6% Propolis | 3.87 | 0.09 | 3.16 | 0.24 | 3.08 | 0.35 |
| 6.6% Propolis + 10% Formalin | 3.66 | 0.13 | 2.96 | 0.21 | 2.87 | 0.16 |
| 0.9% Saline + 10% Formalin | 3.5 | 0.19 | 2.71 | 0.37 | 2.58 | 0.57 |
| Pairwise comparisons by Tukey's multiple post hoc procedures | | | | | | |
| 0.9% Saline vs. 10% Formalin | p = 0.9673 | | p = 0.6760 | | p = 1.0000 | |
| 0.9% Saline vs. 6.6% Propolis | p = 0.7040 | | p = 0.9769 | | p = 0.9195 | |
| 0.9% Saline vs. 6.6% Propolis + 10% Formalin | p = 0.9973 | | p = 0.9952 | | p = 0.4988 | |
| 10% Formalin vs. 6.6% Propolis | p = 0.9636 | | p = 0.3547 | | p = 0.9226 | |
| 10% Formalin vs. 6.6% Propolis + 10% Formalin | p = 0.8691 | | p = 0.8711 | | p = 0.5044 | |
| 6.6% Propolis vs. 6.6% Propolis + 10% Formalin | p = 0.5132 | | p = 0.8711 | | p = 0.9226 | |

At the microscopic level, tissues placed in 0.9% saline showed significant cellular swelling (cytoplasmic vacuolization), shrinkage of the nucleus (pyknotic), indistinct cell borders, and poor staining quality. FIG. 8A shows the features which might indicate tissue autolysis. On the other hand, FIGS. 8B-8D shows other fixative agents which could fix tissue samples over different time points. Most tissue samples in 6.6% propolis showed better staining quality, cellular outline, and nuclear and cytoplasmic details than those in the 10% formalin. However, homogenization of connective tissue was observed in some tissue samples placed in 6.6% propolis for 48 hours. The tissue sections of Group P+F had adequate overall morphology and nuclear, cytoplasmic details, and staining quality. Hence, all solutions, except 0.9% saline, could fix the tissue at different times, with 6.6% propolis giving the best results.

The results are consistent with the findings from a study where honey, sugar, and jaggary syrup may be used as alternative natural fixative agents. However, the present examples showed that propolis has superior fixation ability compared to the 10% formalin after 24 hours.

Evaluation of the fixative properties of 20% honey, 20% jaggery, and 20% sugar compared to the 10% formalin was determined. Human gingival tissues were placed in these solutions for 24 hours. Honey and jaggery gave better results than formalin, which aligns with our results as propolis was superior to the 10% formalin. However, contrary to the present disclosure, sugar showed inferior fixation ability compared to 10% formalin [Kuriachan, D.; Suresh, R.; Janardhanan, M.; Savithri, V.; Aravind, T.; Thampy, L. Analysis of Fixative Properties of Three Ecofriendly Substances: A Comparison with Formalin. Oral Maxillofac. Pathol. J. 2017, 8, 79-84, which is incorporated herein by reference in its entirety].

Interestingly, the propolis showed excellent preservation and fixation properties at 12 and 24 hours compared with the formalin. Furthermore, subsequent transfer of the tissue samples placed in propolis to formalin showed better fixation ability than formalin at all time points. These observations suggest propolis could be an emergency fixative solution, especially without formalin. In addition, it was found that local anesthesia showed comparable morphological features as tissues fixed using formalin and can be utilized as an emergency fixative solution [Kasetty, S.; Dwivedi, D.; Ragavendra, T. R.; Kallianpur, S.; Gupta, S.; Prabhakar, N. Comparison of efficacy of local anesthetic solution, distilled water and normal saline as emergency fixatives. J. Oral Maxillofac. Pathol. 2018, 22, 283, which is incorporated herein by reference in its entirety].

Based on the results of the present investigation, propolis is a natural fixative useful in histopathology. Moreover, the propolis can be used as an interim medium to preserve tissue biopsies before formalin fixation. Results showed that propolis enhances the quality of formalin tissue preservation and fixation.

Numerous modifications and variations of the present disclosure are possible in light of the above teachings. It is therefore to be understood that within the scope of the appended claims, the invention may be practiced otherwise than as specifically described herein.

The invention claimed is:

1. A method of fixing a tissue sample, comprising:

treating the tissue sample having a pre-treatment composition with a propolis-containing composition to form a fixed tissue sample having a post-treatment composition;

wherein the propolis-containing composition comprises a propolis extract and at least one liquid;

wherein the propolis extract comprises a resin and a wax;

wherein the at least one liquid comprises propylene glycol and water, and wherein the propolis-containing composition is an oil-in-water emulsion having an average particle size in a range of 5 to 200 nanometers (nm);

wherein, after the treating, two or more amino groups of the proteins in the pre-treatment composition of the tissue sample are crosslinked by the resin and wax in the propolis extract via two or more functional groups selected from the group consisting of an ester group (—COO—), a hydrocarbon group (—$CH_2$—), an alcohol group (—OH), and a carboxylic acid group (—COOH); and wherein the propolis extract is present in the propolis-containing composition at a concentration of 0.1 to 50 weight percent, based on a total weight of the propolis-containing composition.

2. The method of claim 1, wherein the propolis extract is present in the propolis-containing composition at a concentration of 1 to 15 weight percent, based on the total weight of the propolis-containing composition.

3. The method of claim 1, wherein the propolis extract further comprises at least one substance selected from the group consisting of an oil, a pollen, an amino acid, a minerals, a sugar, a B vitamin, a C vitamin, an E vitamin, a flavonoid, a phenol, an aromatic compound, and combinations thereof.

4. The method of claim 3, wherein the propolis extract further comprises at least one substance selected from the group consisting of luteolin, 3-O—[(S)-2-methylbutyroyl] pinobanksin, 6-cinnamylchrysin, 8-[(E)-4-phenylprop-2-en-1-one]-(2R,3S)-2-(3,5-dihydroxyphenyl)-3,4-dihydro-2H-2-benzopyran-5-methoxyl-3,7-diol, 8-[(E)-4-phenylprop-2-en-1-one]-(2S,3R)-2-(3,5-dihydroxyphenyl)-3,4-dihydro-2H-2-benzopyran-5-methoxyl-3,7-diol, and 8-[(E)-4-phenylprop-2-en-1-one]-(2R,3S)-2-(3-methoxyl-4-hydroxyphenyl)-3,4-dihydro-2H-2-benzopyran-5-methoxyl-3,7-diol.

5. The method of claim 3, wherein the propolis extract comprises one or more of the resin at a concentration of 40 to 80 weight percent;

one or more of the oil and wax at a concentration of 20 to 60 weight percent; and one or more of the pollen at a concentration of 1 to weight percent;

each weight percent based on a total weight of the propolis extract.

6. The method of claim 1, wherein each of the resin and wax in the propolis extract has at least one first functional group, and at least one second functional group;

each of the at least one first functional group and the at least one second functional group is selected from the group consisting of an ester group (—COO—), a hydrocarbon group (—CH2-), an alcohol group (—OH), and a carboxylic acid group (—COOH);

at least one first protein in the pre-treatment composition of the tissue sample is bonded to the resin and wax in the propolis extract via the at least one first functional group; and at least one second protein in the pre-treatment composition of the tissue sample is bonded to the same resin and wax in the propolis extract via the at least one second functional group.

7. The method of claim 1, wherein the propolis-containing composition further comprises one or more additives selected from the group consisting of a fixative agent, an emulsifying agent, a buffering agent, a penetration enhancer, a crosslinking agent, a decalcifying agent, a salt, and a stabilizer.

8. The method of claim 7, wherein the fixative agent is at least one selected from the group consisting of formalin, glutaraldehyde, honey, syrup, and jaggery.

9. The method of claim 7, wherein the emulsifying agent is at least one selected from the group consisting of a cationic surfactant, an anionic surfactant, a non-ionic surfactant, and an amphoteric surfactant.

10. The method of claim 7, wherein the emulsifying agent comprises a fatty alcohol sulfate, a fatty alcohol polyoxyalkylene ether, and a fatty acid alkanolamide.

11. The method of claim 7, wherein the buffering agent is at least one selected from the group consisting of sodium phosphate, sodium dihydrogen phosphate, and disodium hydrogen phosphate.

12. The method of claim 7, wherein the salt comprises at least one alkali metal halide selected from the group consisting of sodium chloride, potassium chloride, sodium bromide, potassium bromide, sodium iodide, and potassium iodide.

13. The method of claim 7, wherein the decalcifying agent comprises ethylenediaminetetraacetic acid (EDTA).

14. The method of claim 1, wherein a ratio of the volume of the tissue sample to the volume of the propolis-containing composition is in a range of 1:1 to 1:20.

15. The method of claim 1, further comprising:

staining the fixed tissue sample with at least one stain selected from the group consisting of a hematoxylin and eosin stain, a reticulin stain, a trichrome stain, a periodic acid-schiff stain, a desmin stain, a TTF1 stain, a CD3 stain, and a PAX8 stain.

16. The method of claim 1, wherein the average particle size of the oil-in-water emulsion is in a range of 50 to 150 nm.

* * * * *